(12) United States Patent
Cho et al.

(10) Patent No.: US 8,815,545 B2
(45) Date of Patent: *Aug. 26, 2014

(54) CORYNEBACTERIA STRAIN HAVING ENHANCED 5'-XANTHOSINE MONOPHOSPHATE PRODUCTIVITY AND A METHOD OF PRODUCING 5'-XANTHOSINE MONOPHOSPHATE USING THE SAME

(75) Inventors: Jinman Cho, Gyeonggi-do (KR); Hye Won Kim, Gyeonggi-do (KR); Jinman Lee, Seoul (KR); Ji-Hye Lee, Gyeonggi-do (KR); Yoon Seok Oh, Gyeonggi-do (KR); Jang Hee Park, Gyeonggi-do (KR)

(73) Assignee: CJ CheilJedang Corporation, Seoul (KR)

( * ) Notice: Subject to any disclaimer, the term of this patent is extended or adjusted under 35 U.S.C. 154(b) by 226 days.

This patent is subject to a terminal disclaimer.

(21) Appl. No.: 13/140,321

(22) PCT Filed: Dec. 17, 2009

(86) PCT No.: PCT/KR2009/007559
§ 371 (c)(1),
(2), (4) Date: Jun. 16, 2011

(87) PCT Pub. No.: WO2010/071367
PCT Pub. Date: Jun. 24, 2010

(65) Prior Publication Data
US 2011/0300582 A1    Dec. 8, 2011

(30) Foreign Application Priority Data
Dec. 17, 2008  (KR) .................. 10-2008-0128847

(51) Int. Cl.
C12P 19/30   (2006.01)
C12N 1/12    (2006.01)
C12N 9/04    (2006.01)
C12P 19/32   (2006.01)

(52) U.S. Cl.
CPC ............... *C12N 9/0006* (2013.01); *C12P 19/32* (2013.01)
USPC ........................................... 435/89; 435/252.1

(58) Field of Classification Search
None
See application file for complete search history.

(56) References Cited

U.S. PATENT DOCUMENTS

2002/0028490 A1   3/2002  Molenaar et al.
2013/0095529 A1*  4/2013  Cho et al. ................ 435/88

FOREIGN PATENT DOCUMENTS

JP   2000-270888   10/2000
JP   2007-512850    5/2007

(Continued)

OTHER PUBLICATIONS

Inui et al., Transcriptional profiling of *Corynebacterium glutamicum* metabolism during organic acid production under oxygen deprivation conditions, Microbiology (2007), vol. 153, No. 8, pp. 2491-2504.*

(Continued)

*Primary Examiner* — Alexander Kim
(74) *Attorney, Agent, or Firm* — Lathrop & Gage LLP; Brian C. Trinque; Andrew T. Wilkins

(57) ABSTRACT

Disclosed is a novel microorganism which has a malate dehydrogenase activity higher than that of a wild-type. Also, a recombinant vector which has the structure shown in the cleavage map of FIG. 1, a *Corynebacteria* strain transformed therewith, and a method of producing 5'-xanthosine monophosphate by culturing the transformed strain are disclosed.

6 Claims, 1 Drawing Sheet

(56) References Cited

FOREIGN PATENT DOCUMENTS

| | | | | |
|---|---|---|---|---|
| KR | 10-2000-0076897 A | 12/2000 | | |
| KR | 10-2002-0057470 A | 7/2002 | | |
| KR | 10-2004-0014489 A | 2/2004 | | |
| KR | 10-2008-0025355 A | 3/2008 | | |
| KR | 10-2009-0080654 A | 7/2009 | | |
| WO | WO 0200907 | * | 1/2002 | ............. C12N 15/75 |
| WO | 2008033001 | | 3/2008 | |

OTHER PUBLICATIONS

O69282 (last viewed on Jun. 27, 2013).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
A. Maruyama et al., "ATP production from adenine by a self-coupling enzymatic process: High-level accumulation under ammonium-limited conditions", Biosci. Biotechnol. Biochem. 65 (3):644-650, 2001.
S. Mitsuhashi, et al., "Disruption of Malate:Quinone Oxidoreductase Increases L-Lysine Production by *Corynebacterium glutamicum*", Biosci. Biotechnol. Biochem. 70 (11):2803-2806, 2006.
M. E. Van Der Rest, et al., "Functions of the Membrane-Associated and Cytoplasmic Malate Dehycrogenase in the Citric Acid Cycle of *Escherichia coli*", Journal of Bacteriology 182 (24):6892-6899, 2000.
International Search Report and Written Opinion from PCT/KR2009/007559, dated Sep. 7, 2010.
Molenaar et al., (1998), Biochemical and Genetic Characterization of the membrane-associated malate dehydrogenase (acceptor) from *Corynebacterium glutamicum*, European Journal of Biochemistry, 254:395-403.

* cited by examiner

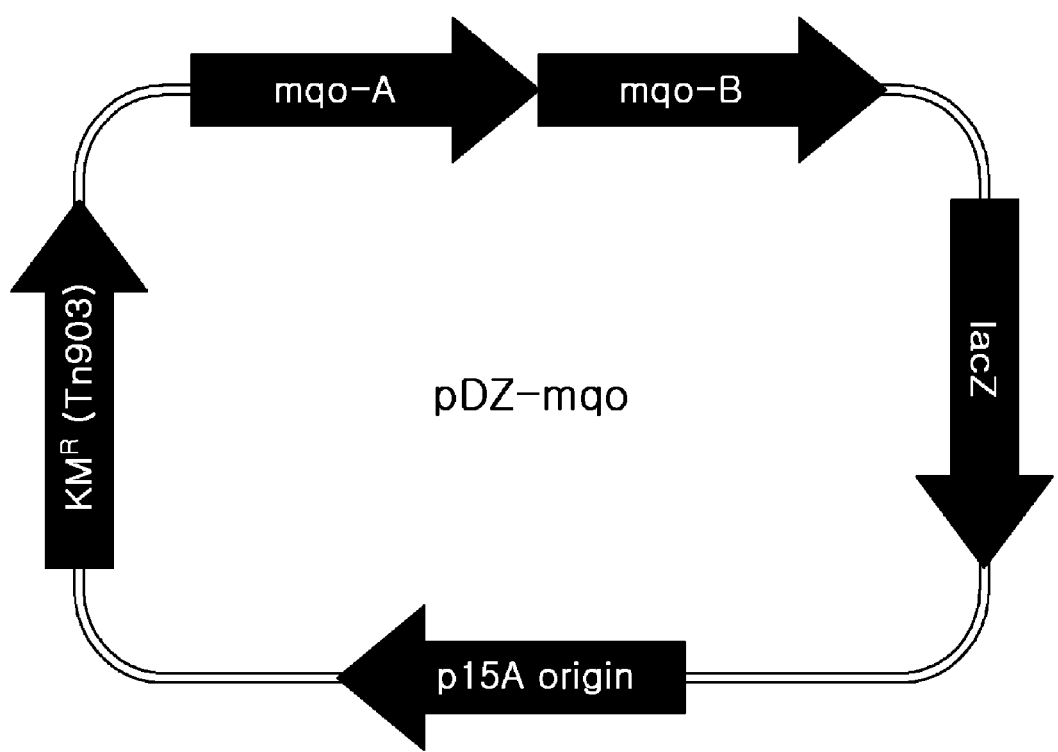

CORYNEBACTERIA STRAIN HAVING ENHANCED 5'-XANTHOSINE MONOPHOSPHATE PRODUCTIVITY AND A METHOD OF PRODUCING 5'-XANTHOSINE MONOPHOSPHATE USING THE SAME

The present application claims the benefit of priority of International Application No. PCT/KR2009/007559, filed Dec. 17, 2009, which claims priority to Korean Patent Application No. 10-2008-0128847, filed Dec. 17, 2008. The entire contents of each of the above documents are incorporated herein by reference.

TECHNICAL FIELD

The present invention relates to a recombinant vector, having the structure shown in the cleavage map of FIG. 1 which carries a gene of SEQ ID NO. 7 and a *Corynebacteria* strain, transformed with the recombinant vector, having higher than the endogenous malate dehydrogenase activity. Also, the present invention is concerned with a method of producing 5'-xanthosine monophosphate using the *Corynebacteria* strain.

BACKGROUND ART

5'-Guanosine monophosphate (hereinafter referred to as "GMP") is a food additive widely used as a flavor enhancer, like inosine monophosphate (hereinafter referred to as "IMP"). GMP elicits an umami taste and its use is dependent on monosodium glutamate (MSG) also being used. It is often used in synergy with IMP to increase the intensity of the umami taste of MSG.

Examples of the methods for the preparation of GMP known thus far include (1) the enzymatic degradation of yeast RNA, (2) direct microorganism fermentation to GMP, (3) microorganism fermentation to guanosine, followed by chemical phosphorylation, (4) microorganism fermentation to guanosine, followed by enzymatic phosphorylation, (5) microorganism fermentation to xanthosine 5'-monophosphate (hereinafter referred to as "XMP"), followed by conversion into GMP by a *corynebacteria* strain, and (6) microorganism fermentation to XMP, followed by conversion of XMP into GMP by *Escherichia coli* which has aminase activity. Of them, method (1) has difficulties of material supply and is economically non-beneficial and method (2) suffers from the disadvantage of being of low yield due to the membrane permeability of GMP. Thus, the other methods are widely used in industrial applications.

For the method in which XMP is produced and converted into GMP, it is critical to increase XMP productivity. For example, Korean Patent Application No. 10-1991-018016 discloses an XMP aminase-inactive strain capable of producing XMP in high yield, which is semi-auxotrophic for adenine and guanine, tolerant of guanosine analoges and very susceptible to lysozyme, an enzyme which destroying cell walls. Korean Patent Application No. 10-2001-000513 discloses a strain of *Corynebacterium ammoniagenes* which can directly accumulate XMP at high concentration in a culture medium and a method of producing XMP using the same. The strain is prepared by irradiating the mother microorganism with UV light, treating with the mutagen N-methyl-N'-nitro-N-nitrosoguanidine (NTG), and selecting a mutant tolerant of norvaline, an analog of valine which affects the biosynthesis of XMP. Korean Patent Application No. 10-2008-006537 describes a method of increasing XMP yield in which purN and purH, genes involved in the biosynthesis of XMP, are modified.

On the other hand, ATP productivity leads to XMP yield because ATP is involved in the biosynthesis of XMP. Also, The activity of malate dehydrogenase has a great influence on the production of ATP. However, nowhere are microorganisms and methods which are designed to enhance malate dehydrogenase activity for increasing XMP production yields mentioned in previous documents.

Keeping in the mind that it is important to increase the ATP productivity of the XMP-producing strain, the present inventors conducted intensive research and found a gene which is responsible for the increase. Also, it was found that a *Corynebacteria* strain transformed with a recombinant vector carrying two copies of the gene in tandem, could produce XMP in high yield.

DISCLOSURE OF INVENTION

Technical Problem

It is therefore an object of the present invention to provide a *Corynebacteria* strain having higher than the endogenous malate dehydrogenase activity.

It is another object of the present invention to provide a recombinant vector having the structure shown in the cleavage map of FIG. 1 which carries the gene of SEQ ID NO. 7.

It is a further object of the present invention to provide a *Corynebacteria* strain transformed with the recombinant vector.

It is still a further object of the present invention to provide a method of producing XMP by culturing the transformed microorganism and obtaining XMP from the culture.

Solution to Problem

In accordance with an aspect thereof, the present invention is directed to a *corynebacteria* strain with enhancements over endogenous malate dehydrogenase activity. Preferably, the *corynebacteria* strain of the present invention is modified to have malate dehydrogenase activity higher than endogenous activity, resulting in an enhancement in XMP productivity.

The term "malate dehydrogenase", as used herein, means an enzyme that catalyzes the conversion of malate into oxaloacetate by dehydrogenation. This enzyme is found in a very broad spectrum of living organisms with the accompaniment of lactate dehydrogenase and requires DPN and NAD as cofactors for its activity, these usually accompanying lactate dehydrogenase. In the *corynebacteria* strain according to the present invention, the malate dehydrogenase activity is increased to produce XMP in higher yield.

As used herein, the term "endogenous activity" is intended to refer to the enzyme activity of interest in a wild-type microorganism. The term "higher than endogenous activity" means increased enzyme activity compared to the activity of the endogenous variety, whether resulting from an activity increase by the enzyme itself or by an endogenous gene or a foreign gene. For example, an increase in enzyme activity may be achieved by any method well known in the art, including, but not limited to, increasing or decreasing the number of gene copies, replacing, modifying or mutating a promoter of interest, etc.

The target enzyme malate dehydrogenase whose activity is sought to be increased according to the present invention is encoded by the mqo gene of *Corynebacteria*. As long as it is biologically identical or correspondends to the mqo gene, any derivative or analog may be used in the present invention. That is, if its activity is substantially the same as or similar to that of the mqo gene, any gene falling within the range of the mqo gene is useful in the present invention. Advantageously, the gene useful in the present invention shares at least 70%, more preferably at least 80%, even more preferably at least 90%, even far more preferably at least 95% and most preferably at least 98% homology with the sequence of the mqo gene. More advantageously, the malate dehydrogenase is encoded by the nucleotide sequence of SEQ ID NO.: 7. The increase of gene copies can be achieved by the introduction of exogenous genes and/or the amplification of endogenous genes. The number of gene copies may be readily determined by those skilled in the art according to need and purpose. The amplification of the endogenous gene can also be conducted using a method known in the art, for example, by culturing in a suitable selective medium under pressure. In a preferred example, a vector carrying a gene coding for malate dehydrogenase is introduced into a *corynebacteria* strain to generate a transformed microorganism with an enhancement over the endogenous activity.

As long as it is known in the art and belongs to the *corynebacteria* genus, any strain may be used in the present invention without limitation. Preferably, examples of the *corynebacteria* strain useful in the present invention include *Corynebacterium ammoniagenes*, *Corynebacterium glutamicum*, *Brevibacterium flavum*, and *Brevibacterium lactofermentum*, but are not limited thereto. In detail, among the *corynebacteria* strains are *Corynebacterium ammoniagenes* ATCC6872, *Corynebacterium thermoaminogenes* FERM BP-1539, *Corynebacterium glutamicum* ATCC 13032, *Corynebacterium glutamicum* R, *Brevibacterium flavum* ATCC 14067, *Brevibacterium lactofermentum* ATCC 13869 and derivatives thereof. Preferred is *Corynebacterium ammoniagenes* KCJ-1304 transformed from *Corynebacterium ammoniagenes* KCCM-10530.

In accordance with another aspect thereof, the present invention is directed into a recombinant vector having the structure shown in the cleavage map of FIG. 1, which carries the gene of SEQ ID NO. 7.

The gene of SEQ ID NO. 7 has a wild-type nucleotide sequence of an mqo gene from *Corynebacteria*. However, it is obvious that a recombinant vector which carries a derivative or analog of the mqo gene is also useful in the present invention as long as the derivative or analog is biologically identical or correspondends to the mqo gene, as mentioned above. As used herein, the term "mqo gene", an abbreviation of "malate:quinone oxidoreductase" gene, means a gene coding for malate oxaloacetate which functions to oxidize malate to oxaloacetate.

In a preferred embodiment, the present invention provides a recombinant vector carrying the mqo gene of SEQ ID NO. 7. As long as it carries an mqo gene, any usual recombinant vector can be employed in the present invention without limitation. Preferable is pDZ-mqo. In a preferred example of the present invention, the mqo gene containing SEQ ID NO. 7 was employed to construct a recombinant pDZ-mqo vector (see FIG. 1).

In accordance with a further aspect thereof, the present invention is directed to a *Corynebacteria* strain transformed with a recombinant vector carrying the mqo gene.

The *corynebacteria*-derived mqo gene may be used using a transformation method known in the art without limitation. Preferably, the mqo gene is cloned in a vector for use in transformation into cells.

Any method may be employed for transformation if it is known in the art. As used herein, the term "transformation" is the genetic alteration of a cell resulting from the uptake, genomic incorporation and expression of foreign DNA. Typical transformation methods include $CaCl_2$ precipitation, a Hanahan method in which the effect of $CaCl_2$ precipitation is improved in combination with DMSO (dimethyl sulfoxide), electroporation, calcium phosphate transfection, protoplast fusion, silicon carbide fiber-mediated transformation, agrobacterium-mediated transformation, PEG-mediated transformation, dextran sulfate, lipofectamine, and desiccation/inhibition-mediated transformation. Transformation with pDZ-mqo in accordance with the present invention is not limited to the examples of transformation, but can be achieved using any method known in the art without limitation.

The term "vector", as used herein, means a DNA molecule used as a vehicle to transfer foreign genetic material into a suitable host cell and is a DNA construct containing regulatory elements which allow a transgene to do recombination with a host genome. Preferably, the recombinant vector carrying the mqo vector in accordance the present invention may have the structure shown in the cleavage map of FIG. 1. The vector represented by the cleavage map of FIG. 1 may be introduced into *corynebacteria* sequentially or simultaneously. In accordance with a preferred embodiment of the present invention, the recombinant vector is transformed into *Corynebacterium ammoniagenes* KCCM-10530 which is then cultured in a selective medium to allow two copies of the mqo gene to incorporate into the genome of the host through homologous recombination, resulting in the generation of a *Corynebacterium ammoniagenes* mutant, named *Corynebacterium ammoniagenes* KCJ-1304. KCJ-1304 was deposited with the Korean Culture Center of Microorganisms (361-221, Honje 1-dong, Seodaemun-gu, Seoul, South Korea) on Dec. 3, 2008 under, accession number KCCM10972P.

*Corynebacterium ammoniagenes* KCJ-1304 has two copies of mqo gene incorporated into the genome of KCCM-10530 resulting from the introduction thereinto of pDZ-mqo having the structure shown in the cleavage map of FIG. 1 and the homologous recombination of two copies of mqo gene with the endogenous gene.

In accordance with a further aspect thereof, the present invention is directed to a method of producing XMP, comprising: culturing the transformed *corynebacteria* strain and obtaining XMP from the culture. In the present invention, XMP is produced in higher yield by the direct fermentation of the transformed microorganism. Preferably, the transformed microorganism is the *corynebacteria* strain which is enhanced in malate dehydrogenase activity over the endogenous activity. The mqo gene of the recombinant vector is preferably incorporated into the genome of the transformed microorganism which can thus produce XMP in high yield. In a preferred embodiment, the microorganism is *Corynebacterium ammoniagenes* KCCM10972P.

Any medium known in the art may be used without limitation in culturing the strain capable of producing XMP. Preferably, the medium contains glucose as a carbon source and optionally various other carbon sources. For use in culturing a microorganism of interest, a medium must meet requirements for the growth of the microorganism. Culture media for *corynebacteria* strains are known in the art (e.g., Manual of Methods for General Bacteriology. American Society for Bacteriology. Washington D.C., USA, 1981). Examples of the carbon sources useful for *corynebacteria* strains include sugars and carbohydrates such as glucose, saccharose, lactose, fructose, maltose, starch, cellulose, etc., oils and lipids such as soybean oil, sunflower oil, castor oil, coconut oil, etc., fatty acids such as palmitic acid, stearic acid, linolenic acid, etc., alcohols such as glycerol, ethanol, etc., and organic acids such as acetic acid. These carbon sources may be used individually or in combination. Organic materials such as peptone, yeast extract, beef extract, malt extract, corn steep liquor, soybean, etc., urea, and inorganic compounds such as ammonium chloride, ammonium phosphate, ammonium carbonate and ammonium nitrate may be used individually or in combination as nitrogen sources in the medium. Potassium dihydrogen phosphate or dipotassium hydrogen phosphate, or corresponding sodium salts may be useful as phosphorus sources. In addition, the culture medium may contain metal salts such as magnesium sulfate, iron sulfate, etc. Further, amino acids and/or vitamins may be required as essential elements. The culture medium may also contain suitable precursors. These materials may be added to a medium in a batch manner or continuous manner.

The culture medium may be adjusted in pH by basic compounds such as sodium hydroxide, potassium hydroxide, ammonia, etc. or acid compounds such as phosphoric acid or sulfuric acid. An antifoaming agent such as fatty acid polyglycol ester may be used to prevent the generation of bubbles during the culturing. The medium may be aerated with oxygen or oxygen-containing gas (e.g., air) to maintain an aerobic condition or with nitrogen, hydrogen or carbon dioxide gas to maintain an anaerobic condition. Culturing temperature is usually maintained at 20° C.~45° C., and preferably at 30° C.~35° C. Culturing is continued until the maximum amount of XMP is obtained. In this regard, a time period of from 10 to 160 hours is required.

The 5XMP thus produced may be secreted into the culture medium or remain within the cell. The method of producing XMP in accordance with the present invention comprises recovering XMP from the cells or the culture medium. For the recovery of XMP from cells or culture media, any method well known in the art may be utilized. Examples of such methods include filtration, anionic exchange chromatography, crystallization, and HPLC, but are not limited thereto.

As used herein, the term "5'-xanthosine monophosphate" is an intermediate in nucleic acid biosynthesis and is of physiological significance in animals and plants. Thus, it finds applications in a variety of fields including the food industry, the pharmaceutical industry and the medical industry. Xanthosine monophosphate are food additives used as nucleic acid-based flavor enhancers to provide the taste of mushroom particularly in synergy with MSG. XMP is an intermediate in purine metabolism, formed from IMP, forming GMP. When using the transformed microorganism in accordance with the present invention, XMP can be produced in a high yield which is found to be improved by about 6% compared to conventional microorganisms.

Advantageous Effects of Invention

Thanks to improved malate dehydrogenase activity, the transformed *corynebacteria* strain of the present invention produces XMP in higher yield than do conventional microorganisms.

BRIEF DESCRIPTION OF DRAWINGS

FIG. 1 is a schematic diagram showing the structure of the recombinant vector pDZ-mqo in which two copies of an mqo gene are inserted into a pDZ vector.

MODE FOR THE INVENTION

A better understanding of the present invention may be obtained through the following examples which are set forth to illustrate, but are not to be construed as limiting the present invention.

EXAMPLE 1

Cloning of the XMP-Producing Strain
*Corynebacterium ammoniagenes*
KCCM-10530-Derived Mqo and Construction of
Recombinant Vector (pDZ-Mqo) for Genomic
Incorporation The nucleotide sequence of the mqo gene (NCBI ID 3345228) was obtained from data from the NIH GenBank. Based on the sequence, two pairs of primers (SEQ ID NOS. 1 to 4) were synthesized.

While the genome of *Corynebacterium* KCCM-10530 served as a template, PCR was conducted in the presence of the high-fidelity DNA polymerase PfuUltra™ (Stratagene) using the primers of SEQ ID NOS. 1 to 4, with 25 cycles of denaturing at 95° C. for 30 sec, annealing at 55° C. for 30 sec and extension at 68° C. for 2 min. The PCR products thus obtained were two copies of the mqo gene, each 2.1 kb long (mqo-A, mqo-B), which were amplified using two sets of SEQ ID NOS: 1 and 2, and SEQ ID NOS: 3 and 4, respectively.

```
                                          SEQ ID NO: 1
          gctctagaATCGGTCATTCCATGAACCC;

SEQ ID NO: 2
          cgcggatccCATCGATATCGCCAACTCCA;

SEQ ID NO: 3
          cgcggatccATCGGTCATTCCATGAACCC;

SEQ ID NO: 4
          gctctagaCATCGATATCGCCAACTCCA;
```

After being treated with suitable restriction enzymes (mqo-A: XbaI+BamHI, mqo-B: BamHI+XbaI), the PCR products mqo-A and mqo-B were inserted into the pDZ vector which was previously treated with XbaI and shrimp alkaline phosphotase, through the three-piece junction (see Korean Patent Application No. 10-2007-94433). Finally, a recombinant pDZ-mqo vector in which two copies of the mqo gene were cloned in tandem was obtained. FIG. 1 is a schematic diagram showing the structure of the recombinant pDZ-mqo vector for incorporation into *Corynebacterium* genome.

EXAMPLE 2

Generation of an mqo-Inserted Strain

The pDZ-mqo vector construct was transformed into the KCCM-10530 strain and subjected to homologous recombination with the genome to insert one mqo gene copy at a position adjacent to the mqo gene on the genome. Thus, a novel XMP-producing strain, named *Corynebacterium ammoniagenes* KCJ-1304, which had two copies of the mqo gene on the genome thereof, was obtained. The insertion of two copies of the mqo gene in tandem was identified using PCR using a set of primers (SEQ ID NOS. 5 and 6) which targeted nucleotide sequences upstream and downstream of the two copies of the mqo gene.

SEQ ID NO. 5:
CTTTTCGATGACGCCCAA

SEQ ID NO. 6:
CCACTTTATCGGGTGAGACCA

EXAMPLE 3

Malate Dehydrogenase Activity of the Mqo-Inserted Strain

The XMP-producing *Corynebacterium ammoniagenes* KCJ-1304 prepared in Example 2 was assayed for malate dehydrogenase activity as follows. The strain was inoculated into a medium containing 10 g/l bactopeptone, 5 g/l bacto-beef extract, 5 g/l bacto-yeast extract, 2.5 g/l NaCl, 50 mg/l adenine, and 50 mg/l guanine and incubated at 30° C. for 12 hrs until OD 10 was obtained. 10 mL of the cell culture was recovered, washed twice with buffer comprising 50 mM HEPES, 10 mM potassium acetate, 10 mM $CaCl_2$ and 10 mM $MgCl_2$, and suspended in 1 mL of the same buffer. After interruption using a sonicator, the cell lysate was centrifuged. The supernatant was re-centrifuged to give a pellet which was then suspended in 100 μL of buffer. 10 μL of this suspension was used as an enzyme solution. A reaction buffer was prepared by mixing 50 mM HEPES, 10 mM potassium acetate and 50 μM 2,6-dichloroindolphenol (Cl2Ind). Cl2Ind was thawed and mixed just before reaction. To 980 μL of the reaction mixture were added 10 μL of 100 mM malate as a substrate and 10 μL of the enzyme solution, followed by incubation at 30° C. for 15 min with shaking. The enzyme activity was determined by measuring the concentration of reduced $Cl_2Ind$. $Cl_2Ind$ had an absorption coefficient of 22 cm-1 mM-1 at 600 nm.

TABLE 1

| Strain | KCCM-10530 | KCJ-1304 |
|---|---|---|
| Reduced $Cl_2Ind$(μM) | 15.45 | 20.17 |

As shown in Table 1, KCJ-1304 was observed to increase in malate dehydrogenase activity by 30.6% compared to the mother strain KCCM-10530.

EXAMPLE 4

XMP Production of the mqo-Inserted Strain

The XMP-producing strain *Corynebacterium ammoniagenes* KCJ-1304 prepared in Example 2 was cultured to produce XMP as follows. The mother strain *Corynebacterium ammoniagenes* KCCM-10530 and the mutant KCJ-1304 were inoculated into respective 14 mL tubes, each containing 3 mL of the following seed medium, and incubated at 30° C. for 20 hrs with shaking at 200 rpm. Then, the seed cultures were added in an amount of 0.4 mL to 32 mL of the following production medium (24 mL of main medium+8 mL of medium A) in respective 250 mL corner-baffle flasks, followed by shake culturing at 30° C. and 230 rpm for 96 hrs. Thereafter, the production of 5'-XMP was quantitatively measured using HPLC. The XMP amounts produced from *Corynebacterium ammogenes* KCCM-10530 and KCJ-1304 are given in Table 2, below.

TABLE 2

| Strain | KCCM-10530 | KCJ-1304 |
|---|---|---|
| KCCM-10530 | 28.6 | 30.3 |

Seed Medium: glucose 30 g/l, peptone 15 g/l, yeast extract 15 g/l, NaCl 2.5 g/l, urea 3 g/l, adenine 150 mg/l, guanine 150 mg/l, pH 7.2

Production Medium (main): glucose 80 g/l, magnesium sulfate 10 g/l, ferrous sulfate 20 mg/l, zinc sulfate 10 mg/l, manganese sulfate 10 mg/l, adenine 30 mg/l, guanine 30 mg/l, biotin 100 μg/l, copper sulfate 1 mg/l, thiamine chloride 5 mg/l, calcium chloride 10 mg/l, pH 7.2

Production Medium (medium A): monopotassium phosphate 10 g/l, dipotassium phosphate 10 g/l, urea 7 g/l, ammonium sulfate 5 g/l As is apparent from the data of Table 2, KCJ-1304 was found to increase in XMP production by 1.7 g/l, corresponding to 5.9% increase, compared to the mother strain KCCM-10530.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An isolated *Corynebacteria ammoniagenes* strain, which strain has a malate:quinone oxidoreductase activity higher than that of a wild-type *Corynebacteria ammoniagenes*, wherein the higher MQO activity is achieved by increasing the number of mqo gene copies encoding the malate dehydrogenase, or replacing or modifying a promoter of an mqo gene, wherein said mqo gene is the *Corynebacteria ammoniagenes* mqo gene.

2. The isolated *Corynebacteria ammoniagenes* strain according to claim 1, wherein the strain has two copies of the *Corynebacteria ammoniagenes* mqo (malate:quinone oxidoreductase) gene incorporated into the *Corynebacteria ammoniagenes* genome.

3. An isolated *Corynebacterium ammoniagenes* strain, the strain being the *Corynebacterium ammoniagenes* strain deposited under accession number KCCM10972P.

4. A method of producing 5'-xanthosine monophosphate, comprising:
culturing an isolated *Corynebacteria ammoniagenes* strain having a malate:quinone oxidoreductase (MQO) activity higher than that of wild-type *Corynebacteria ammoniagenes*, wherein the higher MQO activity is achieved by increasing the number of mqo gene copies encoding the malate dehydrogenase, or replacing or modifying a promoter of an mqo gene; and obtaining 5'-xanthosine monophosphate produced by the isolated *Corynebacteria ammoniagenes* strain from the culture,
wherein said mqo gene is the *Corynebacteria ammoniagenes* mqo gene.

5. The method according to claim 4, wherein the isolated *Corynebacteria ammoniagenes* strain has two copies of the mqo (malate:quinone oxidoreductase) gene incorporated into the genome of *Corynebacteria ammoniagenes*.

6. A method of producing 5'-xanthosine monophosphate, comprising:
culturing the *Corynebacterium ammoniagenes* strain deposited under accession number KCCM10972P and obtaining 5'-xanthosine monophosphate from the culture.

* * * * *

SEQUENCE LISTING

```
<160> NUMBER OF SEQ ID NOS: 7

<210> SEQ ID NO 1
<211> LENGTH: 28
<212> TYPE: DNA
<213> ORGANISM: Artificial Sequence
<220> FEATURE:
<223> OTHER INFORMATION: forward primer for mqo-A

<400> SEQUENCE: 1
gctctagaat cggtcattcc atgaaccc                                    28

<210> SEQ ID NO 2
<211> LENGTH: 29
<212> TYPE: DNA
<213> ORGANISM: Artificial Sequence
<220> FEATURE:
<223> OTHER INFORMATION: reverse primer for mqo-A
```

<400> SEQUENCE: 2
cgcggatccc atcgatatcg ccaactcca                              29

<210> SEQ ID NO 3
<211> LENGTH: 29
<212> TYPE: DNA
<213> ORGANISM: Artificial Sequence
<220> FEATURE:
<223> OTHER INFORMATION: forward primer for mqo-B

<400> SEQUENCE: 3
cgcggatcca tcggtcattc catgaaccc                              29

<210> SEQ ID NO 4
<211> LENGTH: 28
<212> TYPE: DNA
<213> ORGANISM: Artificial Sequence
<220> FEATURE:
<223> OTHER INFORMATION: reverse primer for mqo-B

<400> SEQUENCE: 4
gctctagaca tcgatatcgc caactcca                               28

<210> SEQ ID NO 5
<211> LENGTH: 18
<212> TYPE: DNA
<213> ORGANISM: Artificial Sequence
<220> FEATURE:
<223> OTHER INFORMATION: forward primer for detecting mqo

<400> SEQUENCE: 5
cttttcgatg acgcccaa                                          18

<210> SEQ ID NO 6
<211> LENGTH: 21
<212> TYPE: DNA
<213> ORGANISM: Artificial Sequence
<220> FEATURE:
<223> OTHER INFORMATION: reverse primer for detecting mqo

<400> SEQUENCE: 6
ccactttatc gggtgagacc a                                      21

<210> SEQ ID NO 7
<211> LENGTH: 1503
<212> TYPE: DNA
<213> ORGANISM: Corynebacterium ammoniagenes

<400> SEQUENCE: 7
atgtcagatt ccccgaagaa cgcaccgagg attaccgatg aggcagatgt agttctcatt    60
ggtgccggta tcatgagctc cacgctgggt gcaatgctgc gtcagctgga gccaagctgg   120
actcagatcg tcttcgagcg tttggatgga ccggcacaag agtcgtcctc cccgtggaac   180
aatgcaggaa ccggccactc tgctctatgc gagctgaact acaccccaga ggttaagggc   240
aaggttgaaa ttgccaaggc tgtaggaatc aacgagaagt tccaggtttc ccgtcagttc   300
tggtctcacc tcgttgaaga gggagtgctg tctgatccta aggaattcat caaccctgtt   360
cctcacgtat ctttcggcca gggcgcagat caggttgcat acatcaaggc tcgctacgaa   420
gctttgaagg atcacccact cttccagggc atgacctacg ctgacgatga agctaccttc   480
accgagaagc tgcctttgat ggcaaagggc cgtgacttct ctgatccagt agcaatctct   540

-continued

```
tggatcgatg aaggcaccga catcaactac ggtgctcaga ccaagcagta cctggatgca    600
gctgaagttg aaggcactga aatccgctat ggccacgaag tcaagagcat caaggctgat    660
ggcgcaaagt ggatcgtgac cgtcaagaac gtacacactg gcgacaccaa gaccatcaag    720
gcaaacttcg tgttcgtcgg cgcaggcgga tacgcactgg atctgcttcg cagcgcaggc    780
atcccacagg tcaagggctt cgctggattc ccagtatccg gcctgtggct tcgttgcacc    840
aacgaggaac tgatcgagca gcacgcagcc aaggtatatg gcaaggcatc tgttggcgct    900
cctccaatgt ctgttcctca ccttgacacc cgcgttatcg agggtgaaaa gggtctgctc    960
tttggaccct acggtggctg gacccctaag ttcttgaagg aaggctccta cctggacctg    1020
ttcaagtcca tccgcccaga caacattcct tcctaccttg gcgttgctgc tcaggaattt    1080
gatctgacca agtaccttgt cactgaagtt ctcaaggacc aggacaagcg tatggatgct    1140
cttcgcgagt acatgccaga ggcacaaaac ggcgattggg agaccatcgt tgccggacag    1200
cgtgttcagg ttattaagcc tgcaggattc cctaagttcg gttccctgga attcggcacc    1260
accttgatca acaactccga aggcaccatc gccggattgc tcggtgcttc ccctggagca    1320
tccatcgcac cttccgcaat gatcgagctg cttgagcgtt gcttcggtga ccgcatgatc    1380
gagtggggcg acaagctgaa ggacatgatc ccttcctacg gcaagaagct tgcttccgag    1440
ccagcactgt ttgagcagca gtgggcacgc acccagaaga ccctgaagct tgaggaagcc    1500
taa                                                                 1503
```